United States Patent [19]

Parker

[11] 4,367,346

[45] Jan. 4, 1983

[54] METHOD FOR SYNTHESIS OF LONG-CHAIN ALCOHOLS

[75] Inventor: Dane K. Parker, Massillon, Ohio

[73] Assignee: The Goodyear Tire & Rubber Company, Akron, Ohio

[21] Appl. No.: 256,626

[22] Filed: Apr. 23, 1981

[51] Int. Cl.$^3$ .................... C07C 29/136; C07C 51/00
[52] U.S. Cl. .................... 568/884; 260/413; 562/512
[58] Field of Search .................... 568/884; 260/413; 562/512

[56] References Cited

U.S. PATENT DOCUMENTS 4,167,641 9/1979 Welebir .................... 568/884

OTHER PUBLICATIONS

Hunig et al., Chem. Ber., vol 100 (1967) 4010–4026.

*Primary Examiner*—Bernard Helfin
*Attorney, Agent, or Firm*—D. O. Nickey

[57] ABSTRACT

This invention is concerned with the preparation of long-chain carboxylic acids and alcohols from cyclododecanone and acyl chlorides. More specifically, this invention relates to a process for the preparation of 1-triacontanol, $CH_3(CH_2)_{28}CH_2OH$. Triacontanol acts as a growth stimulant on a wide range of plants to increase dry weight gains, water uptake, water use efficiency and protein synthesis in treated plants.

4 Claims, No Drawings

METHOD FOR SYNTHESIS OF LONG-CHAIN ALCOHOLS

BACKGROUND OF THE INVENTION

To the present date, synthesis of long-chain carboxylic acids containing up to about 33 carbon atoms in a straight chain have not proven to be useful economically when applied to large scale production. Most processes involve a keto-acid intermediate. Some older processes show very low yields and involve additions of various half esters, half-acid chlorides (or halides) to organometallic intermediates or beta-keto esters. While some other methods show good yields, they produce contaminated products. One aspect of the present invention is to produce these long-chain carboxylic acids and their alcohols economically with improved yields and purity.

Specifically, the process of this invention provides for the economical synthesis of 1-triacontanol. U.S. Pat. No. 4,150,970 discusses in detail the growth regulating effect of 1-triacontanol for plants.

U.S. Pat. No. 4,167,641 relates to a method for the preparation of long-chain carboxylic acids which can be readily converted to alcohols. However, the disclosed method of synthesis involves many reaction steps and requires extensive manpower and special equipment for purification.

The process of the present invention is designed for preparation of long-chain carboxylic acids and alcohols wherein cyclododecanone is reacted with morpholine in the presence of an acid catalyst to yield 1-morpholino-1-cyclododecene.

The present invention uses this enamine:

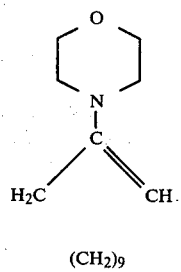

(I)

1-morpholino-1-cyclododecene as a basic starting material. The preparation of 1-morpholino-1-cyclododecene is described by W. Lendle et al in *Chem. Ber.* 100, 3996 (1967).

Compound (I) is reacted with acid halides of the type (II):

(II) Acid Halide wherein Z is a chlorine, bromine, iodine or fluorine radical and X is 0, 1, 2, 3, 4, or 5 to obtain long chain alcohols of type (V) according to the following representative scheme:

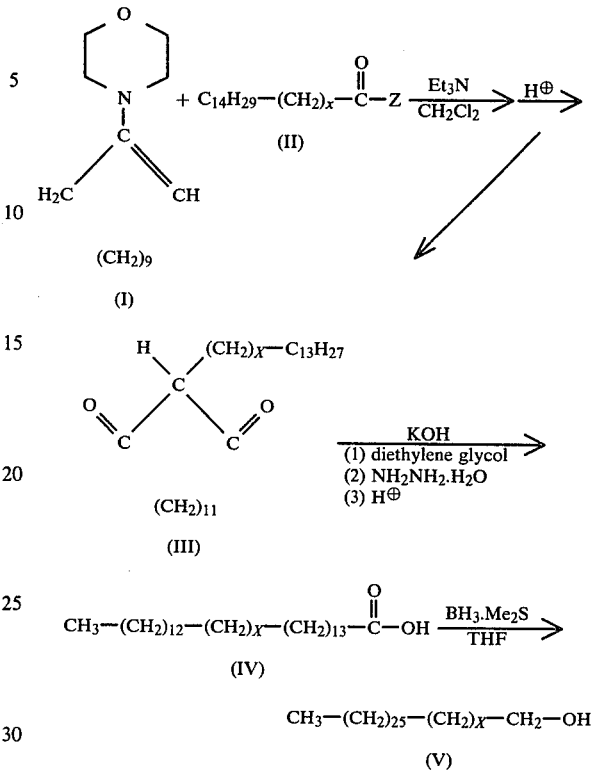

One advantage of the present invention over what is known in the art is that acid chlorides of type (II) are used, which are cheaper and more readily available than lignoceric acid (a linear carboxylic acid containing 24 carbon atoms).

An important difference in the present process over that of U.S. Pat. No. 4,167,641 is evidenced by the different products obtained at the compound (III) stage. A ring expansion has taken place in the present process to yield a 14-member β-diketone with both keto groups in the ring as opposed to no ring expansion in the process of U.S. Pat. No. 4,167,641 and a β-diketone with one keto group external to the ring.

Hünig & Buysch in *Chem. Br.* 100,4010 (1967) describe a method to cleave a 14-membered alkylated ketone in ethanol to yield the sodium salt of 13-keto-triacontanoic acid, however, the process is cumbersome in that multireaction steps are required and yields and purities are only moderate.

The applicant has unexpectedly discovered that the cleavage of the 14-member β-diketone compound (III) can be accomplished with an alkali metal hydroxide in a solvent (i.e. diethylene or triethylene glycol), thus eliminating a separate step for the cleavage reaction in ethanol. Furthermore, it has been discovered that the cleavage and reduction steps can be carried out sequentially in one reaction vessel.

DISCLOSURE OF THE INVENTION

There is disclosed a process for the preparation of long-chain carbon compounds characterized by: (a) reacting cyclododecanone with morpholine in the presence of a catalyst to form 1-morpholino-1-cyclododecene; (b) separating the 1-morpholino-1-cyclododecene and reacting it with an organic acid halide of 15-20 carbon atoms in the presence of a tertiary amine in an organic solvent while maintaining the reaction temperature at 0°-10° C. followed by (c) hydrolysis under acidic conditions, thereafter (d) separating the 2-n-alkyl-cyclotetradecanedione and reacting with a solution of alkali metal hydroxide and diethylene glycol at 90°-110° C. followed by (e) addition of hydrazine hydrate and the reaction mixture is refluxed at 125°-135° C. thereafter (f) the distillate is removed until the temperature of the reaction mixture climbs to 190°-210° C. where it is refluxed for 3 to 20 hours with slow stirring, and then (g) cooled to 110°-125° C. followed by addition of hot (80°-95° C.) water with rapid stirring followed by (h) neutralization with aqueous acid to a pH of 2 to yield the carboxylic acid which is separated and purified by recrystallization which is then (i) dissolved in tetrahydrofuran under an inert atmosphere and has added thereto the reducing agent, borane-methyl sulfide complex with stirring and heated to 40°-65° C. for 2 to 3 hours before cooling to ambient temperature followed by the sequential addition of methanol and water to quench excess borane reagent followed by (k) separation and purification of the long chain alcohol.

MORE DETAILED DISCLOSURE

The process of the invention is designed for the preparation of long-chain carboxylic acid which can be readily converted to alcohols. The process uses the enamine, 1-morpholino-1-cyclododecene.

Stearoyl chloride is the preferred linear acid chloride, however, other acid chlorides of 15 to 20 carbon atoms can be utilized in the process of the present invention. Chlorinating agents, such as thionyl chloride and phosphorus pentachloride are preferred, however, other chlorinating agents known in the art can be used.

The preferred tertiary amine is the triethyl amine, however, other compounds which may be utilized include tri-n-propyl amine, tri-n-butyl amine, tri-n-hexyl amine, tri-n-octyl amine, N,N-dimethyl aniline, pyridine and ring substituted pyridines.

Dichloromethane is the preferred organic solvent in the preparation of the β-diketone, however, other organic solvents such as chloroform, carbon tetrachloride, 1,2-dichloroethane, toluene, chlorobenzene and ortho-dichlorobenzene may be used.

Hydrochloric acid is the preferred acid in the preparation of the β-diketone and carboxylic acid, however, any strong aqueous mineral acid may be employed, for example, $H_2SO_4$ and $H_3PO_4$.

KOH is the preferred alkali metal hydroxide, however, sodium hydroxide can be used.

Diethylene glycol is the preferred glycol, however, tetraethylene glycol or triethylene glycol can be used.

Borane-methyl sulfide complex is the preferred reducing agent, however, compounds such as borane tetrahydrofuran complex or other di-borane reagents may be utilized.

The skilled chemist will readily be able to determine the proper molar ratios of the reactants in the process of the present invention. Stoichiometry will determine the molar ratios, however, some excesses may be required to promote the economics of the reaction.

More specifically, cyclododecanone is reacted in a 1:1 to 1:20 molar ratio with morpholine. The preferred ratio being 1:2. A mole ratio of cyclododecanone to TSA is maintained at about 250:1 to 50:1 with the preferred ratio being 125:1. In the preparation of the stearoyl halide the acid is reacted with thionyl chloride in a molar ratio of 1:1 to 1:100 with the preferred mole ratio being 1:1.11. It has been found appropriate to maintain a mole ratio of stearic acid to DMF catalyst at 100:1 to 25:1 with the preferred ratio of 50:1.

The reaction of 1-morpholino-1-cyclododecene, compound I, to the stearoyl halide in the mole ratios of 1:1 to 100:1 has been found to be appropriate. However, a mole ratio of 1.24:1 is preferred. A molar ratio of compound I to triethylamine of 1:1 to 1:100 has been found appropriate with a preferred molar ratio being 1:1.24.

In addition, it has been found that a ratio of stearoyl halide to methylene chloride of 1.22 moles of stearoyl chloride to 250 ml. of methylene chloride is appropriate.

In the reaction of 2-n-hexyldecyl-cyclotetradecanedione with potassium hydroxide a mole ratio of 1:2 to 1:20 is appropriate with a preferred ratio being 1:5. A ratio of the in situ generated potassium salt of 13 keto tricontanoic acid with 85 percent hydrazine hydrate of 1:1 to 1:20 has been found to be appropriate with a more preferred ratio being 1:5.

The 1-triacontanoic acid is reacted with a 10 M solution of borane-dimethylsulfide complex in a mole ratio of 1:1 to 1:100 with a preferred ratio being 1:2.

The following examples are presented to illustrate the invention and are not intended to limit the scope of the present invention. The following examples describe a method for the synthesis of 1-triacontanol.

EXAMPLE I

Preparation of 1-Morpholino-1-Cyclododecene

A two liter three-necked flask was charged with 366 gr. (2.0 moles) cyclododecanone, 348 gr. (4.0 moles) morpholine, 600 ml toluene and 3.0 gr. (0.0158 moles) para-toluene sulfonic acid catalyst. A magnetic stir bar was added along with a few carbon boiling chips. A Dean-Stark water trap and condenser were then attached and the mixture brought to reflux with stirring. After 46 hours reflux, 75 ml. of aqueous phase had been collected. The mixture was then cooled and the excess toluene and morpholine removed at reduced pressure (25–50 mm Hg). The residue was then distilled under vacuum (0.6 mm. Hg) to yield 300.5 gr. of a viscous clear oil, 1-morpholino-1-cyclododecene, b.p. 135°-150° C., 60% yield.

EXAMPLE II

Preparation of Stearoyl Chloride

A two liter three-necked flask was charged with 570 gr. (2.0 moles) stearic acid. The flask was then equipped with a mechanical stirrer, nitrogen inlet and thermometer in a fume hood. The system was then purged with a slow bleed of nitrogen and 163 ml. (265 gr.) 2.23 moles of thionyl chloride and 3 ml. (~0.04 moles) of dimethylformamide catalyst were added. The mixture was slowly warmed over one hour to 65° C. All the solid slowly dissolves during this period to yield a clear yellow liquid (HCl and $SO_2$ evolved). Heat was removed and the mixture was allowed to stand at room temperature overnight under nitrogen. Strip off under vacuum excess thionyl chloride and dimethyl formamide catalyst to obtain 580 gr. of stearoyl chloride (95.7% yield) as a clear brownish liquid.

EXAMPLE III

Preparation of 2-n-hexadecyl-cyclotetradecanedione

A three liter three-necked flask was charged with 356.6 gr. (1.42 moles) of 1-morpholino-1-cyclododecene and 153.5 gr. (1.52 moles) triethylamine. The flask was then equipped with a mechanical stirrer, nitrogen inlet, thermometer and a dropping funnel. A solution of 390.4 gr. (1.22 moles) of stearoyl chloride in 250 ml. of methylene chloride was then placed in the dropping funnel. The reaction flask was cooled to 0°–5° C. and the stearoyl chloride solution added over 5½ to 6 hours with the temperature kept between 5°–10° C. After the addition was complete, the mixture was allowed to stand at room temperature overnight.

This was followed by the addition with stirring of 500 ml. of 5 N hydrochloric acid and 600 ml. of methylene chloride. One-half gram of the phase-transfer catalyst n-hexadecyl-tri-n-butyl phosphonium bromide was then added and the mixture refluxed for two hours to complete the hydrolysis. The methylene chloride layer was then separated out and the solvent allowed to evaporate to yield 615.5 gr. of the crude product. Gas chromatographic analysis indicates a composition of approximately 69% diketone, 17.5% cyclododecanone and 2.5% stearic acid. The addition of the phase-transfer catalyst, n-hexyldecyl tri-n-butyl phosphonium bromide was used to promote the reaction, however, the reaction will proceed without a catalyst.

EXAMPLE IV

Preparation of 1-Triacontanoic Acid

A two-liter three-necked flask equipped with a mechanical stirrer, thermometer, nitrogen inlet and dropping funnel was charged with 126.15 gr. (~0.194 moles) crude 2-n-hexadecyl-cyclotetradecanedione, 350 ml. diethylene glycol, 66.0 gr. (~1.0 mole) potassium hydroxide pellets and 5 ml. ethanol. The mixture was then warmed under nitrogen with stirring to 110° C. for 1½ to 2 hours. After this period, 60 ml. (~1.0 mole) of 85% hydrazine hydrate was added all at once and the temperature raised to reflux (~127°–132° C.) for 2 hours. A Dean-Stark trap was then attached. Distillate was slowly removed until the temperature of the reaction mixture had climbed to 195°–205° C. Once at this temperature, the trap was removed and the mixture refluxed at this temperature ~4–24 hours with slow stirring. The reaction mixture was then cooled to 110°–125° C. and 750 ml. of hot water (80°–90° C.) was carefully added with rapid stirring. This was followed by the addition over 10 minutes of 250 ml. of 5 N hydrochloric acid. The pH of the mixture at this point is between 0 and 2. The crude 1-triacontanoic acid crystallizes as a fine powder upon cooling the vigorously stirred mixture to room temperature. Gas chromatographic analysis of the crude product indicated a composition of approximately 55% 1-triacontanoic acid, 5.4% 13-keto-1-triacontanoic acid, 10% cyclododecane and 20% stearic acid. The crude 1-triacontanoic acid can be conveniently purified by recrystallization from methyl ethyl ketone. 80.66 gr. isolated after recrystallization, 91.8% yield (based on 69% purity of starting 2-n-hexadecyl-cyclotetradecanedione). The addition of 5 ml of ethanol was used to promote the reaction, however, the reaction will proceed without the addition of ethanol. Applicant candidly discloses the use of ethanol as the best mode in synthesizing the 1-triacontanoic acid.

EXAMPLE V

A five-liter three-necked flask equipped with a mechanical stirrer, nitrogen inlet, septum inlet, thermometer and condenser was charged with 182.0 gr. (0.402 moles) recrystallized 1-triacontanoic acid and 1900 ml. tetrahydrofuran. The system was continuously purged with a slow nitrogen stream while being warmed to 35° C. At this temperature, 75 ml (~0.75 moles) of 10 M borane-methyl sulfide complex was added over a thirty minute period via a long needle syringe. After the addition, the mixture was stirred three hours at 45° C. then warmed to 65° C. for one hour before cooling to room temperature (~25° C.) 250 ml. of methanol was then carefully added over thirty minutes followed by the addition of 150 ml. of water over fifteen minutes. The quenched mixture was then poured into excess of cold water and left to stand in a fume hood overnight. The crude product was filtered off and dried in a circulating air oven at 50° C. to yield 147.0 gr. crude 1-triacontanol. Gas chromatographic analysis of the crude product indicated a composition of 89.3% 1-triacontanol, 1.5% octacosanol and 5.2% 1,13-triacontandiol.

The crude 1-triacontanol (89.3% purity) could be readily purified by placing 50.0 gr. of crude material in a cellulose extraction thimble and extracting it continuously in a soxhlet apparatus with boiling hexane (1250 ml. hexane volume). After ~2–3 hours extraction all the triacontanol had been removed from the thimbles. A magnetic stir bar was then added to the hot hexane solution and the mixture stirred in air until reaching ambient conditions. During this period 1-triacontanol crystallized out of the mixture. 35.3 gr. of 1-triacontanol were isolated by filtration and analyzed to be 96.6% pure 1-triacontanol, 1.3% octacosanol and 0.5% 1,13-triacontanediol.

In a purification of 1-triacontanol by recrystallization a ratio of 50 gr. of crude 1-triacontanol into 800 ml. to 3000 ml. of normal hexane is appropriate with the preferred amount being 1,250 ml. The solution is cooled slowly with stirring to room temperature and the recrystallized 1-triacontanol is filtered off.

It is apparent from the examples hereinabove that the invention includes a number of proceses and steps for the formation and treatment of long-chain carboxylic acids.

While the preferred embodiments of the invention have been described the invention is not to be construed as limited thereby accept the same may be included in the following claims.

I claim:

1. A process for the preparation of long-chain carbon compounds characterized by: (a) reacting cyclododecanone with morpholine in the presence of a catalyst to form 1-morpholino-1-cyclododecene; (b) separating the 1-morpholino-1-cyclododecene and reacting it with an organic acid halide of the structural formula:

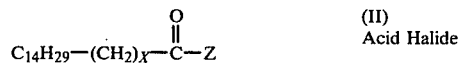

$$C_{14}H_{29}-(CH_2)_x-\overset{O}{\underset{\|}{C}}-Z \qquad \text{(II)}$$
Acid Halide wherein Z is a chlorine, bromine, iodine or fluorine radical and X is 0, 1, 2, 3, 4, or 5; in the presence of a tertiary amine in an organic solvent while maintaining the reaction temperature at 0°–10° C. followed by (c)

hydrolysis under acidic conditions, thereafter (d) separating the 2-n-alkyl-cyclotetradecanedione and reacting with a solution of alkali metal hydroxide and diethylene glycol at 90°–110° C. followed by (e) addition of hydrazine hydrate and the reaction mixture is refluxed at 125°–135° C. thereafter (f) the distillate is removed until the temperature of the reaction mixture climbs to 190°–210° C. where it is refluxed for 3 to 20 hours with slow stirring, and then (g) cooled to 110°–125° C. followed by addition of hot (80°–95° C.) water with rapid stirring followed by (h) neutralization with aqueous acid to a pH of 2 to yield the carboxylic acid which is separated and purified by recrystallization which is then (i) dissolved in tetrahydrofuran under an inert atmosphere and has added thereto the reducing agent, borane-methyl sulfide complex with stirring and heated to 40°–45° C. for 2 to 3 hours before cooling to ambient temperature followed by the sequential addition of methanol and water to quench excess borane reagent followed by (k) separation and purification of the long-chain alcohol.

2. A process according to claim 1 wherein the organic acid chloride is stearoyl chloride.

3. A process according to claim 1 wherein the alkali metal hydroxide is KOH.

4. A process according to claim 1 wherein the long-chain alcohol is 1-triacontanol.

* * * * *

UNITED STATES PATENT OFFICE
CERTIFICATE OF CORRECTION

PATENT NO. : 4,367,346

DATED : Jan. 4, 1983

INVENTOR(S) : Dane K. Parker

It is certified that error appears in the above-identified patent and that said Letters Patent are hereby corrected as shown below:

Col. 1, Formula at Line 40,

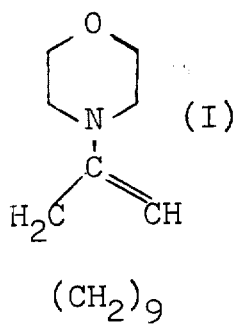   SHOULD BE   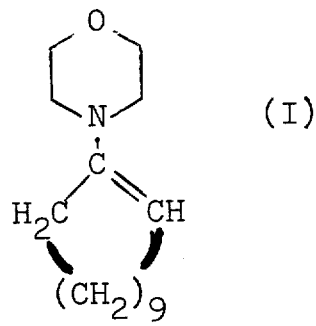

1-morpholino-1-cyclododecene          1-morpholino-1-cyclodecene

Col. 1, Formula (II), Line 60

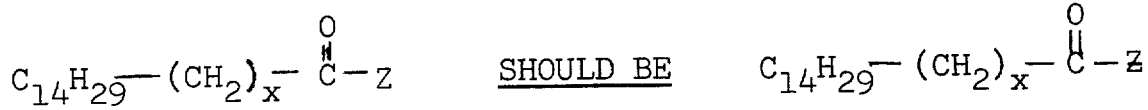

UNITED STATES PATENT OFFICE
CERTIFICATE OF CORRECTION

PATENT NO. : 4,367,346

DATED : Jan. 4, 1983

INVENTOR(S) : Dane K. Parker

It is certified that error appears in the above-identified patent and that said Letters Patent are hereby corrected as shown below:

Column 2, Lines 1-13, Formulae (I) and (II) :

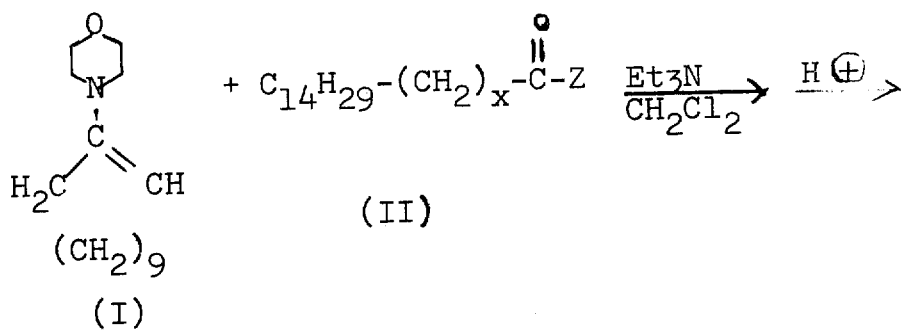

SHOULD BE

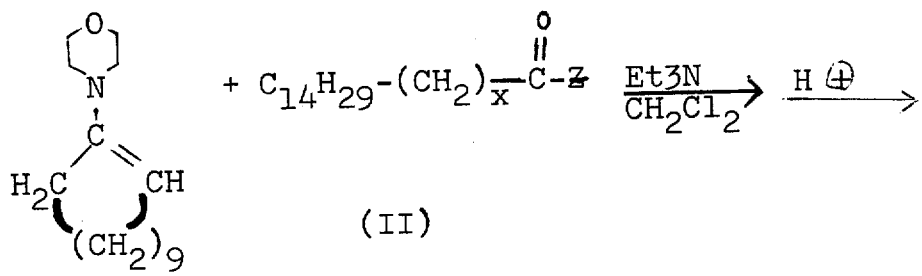

UNITED STATES PATENT OFFICE
CERTIFICATE OF CORRECTION

PATENT NO. : 4,367,346

DATED : Jan. 4, 1983

INVENTOR(S) : Dane K. Parker

It is certified that error appears in the above-identified patent and that said Letters Patent are hereby corrected as shown below:

Column 2, Lines 15-22, Formula (III)

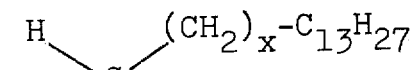

$$\begin{array}{c} H \diagdown \quad \diagup (CH_2)_x - C_{13}H_{27} \\ \quad C \\ O = C \diagdown \diagup C = O \\ (CH_2)_{11} \end{array} \quad \xrightarrow{\begin{array}{l}(1)\ \text{diethylene glycol}\\(2)\ NH_2NH_2 \cdot H_2O\\(3)\ H^+\end{array}}$$

(III)

SHOULD BE

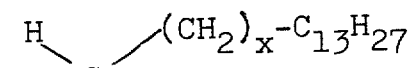

$$\begin{array}{c} H \diagdown \quad \diagup (CH_2)_x - C_{13}H_{27} \\ \quad C \\ O \diagdown \quad \diagup O \\ C \quad C \\ \diagup\!\!\!\diagdown \quad \diagdown\!\!\!\diagup \\ (CH_2)_{11} \end{array} \quad \xrightarrow{\begin{array}{l}(1)\ \text{diethylene glycol}\\(2)\ NH_2NH_2 \cdot H_2O\\(3)\ H+\end{array}} \qquad (III)$$

UNITED STATES PATENT OFFICE
CERTIFICATE OF CORRECTION

PATENT NO. : 4,367,346     Page 4 of 4
DATED : Jan. 4, 1983
INVENTOR(S) : Dane K. Parker It is certified that error appears in the above-identified patent and that said Letters Patent are hereby corrected as shown below:

Column 6, Lines 60-64 - Claim 1.

$$C_{14}H_{29}\text{-}(CH_2)_x\text{-}\overset{\overset{O}{\|}}{C}\text{-}Z \qquad \underline{\text{SHOULD BE}} \qquad C_{14}H_{29}\text{-}(CH_2)_x\text{-}\overset{\overset{O}{\|}}{C}\text{-}\mathbf{Z}$$

(II)                                                   (II)

ACID HALIDE                     ACID HALIDE

Signed and Sealed this

Seventeenth Day of January 1984

[SEAL]

Attest:

GERALD J. MOSSINGHOFF

Attesting Officer        Commissioner of Patents and Trademarks

UNITED STATES PATENT AND TRADEMARK OFFICE
CERTIFICATE OF CORRECTION

PATENT NO. : 4,367,346

DATED : Jan. 4, 1983

INVENTOR(S) : Dane K. Parker

It is certified that error appears in the above-identified patent and that said Letters Patent is hereby corrected as shown below:

Column 2, Lines 1-8, Formula (II) :

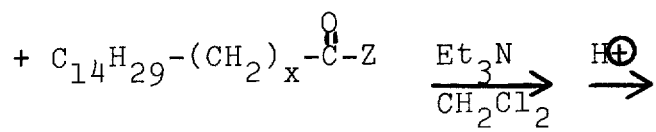

(II)

SHOULD BE

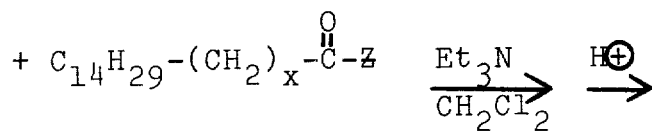

(II)

Column 2, Lines 15-22, Formula (III) :

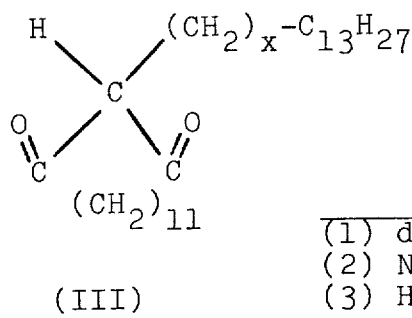

(III)

(1) diethylene glycol
(2) $NH_2NH_2 \cdot H_2O$
(3) $H^{\oplus}$

UNITED STATES PATENT AND TRADEMARK OFFICE
CERTIFICATE OF CORRECTION

PATENT NO. : 4,367,346

DATED : Jan. 4, 1983

INVENTOR(S) : Dane K. Parker

It is certified that error appears in the above-identified patent and that said Letters Patent is hereby corrected as shown below:

SHOULD BE

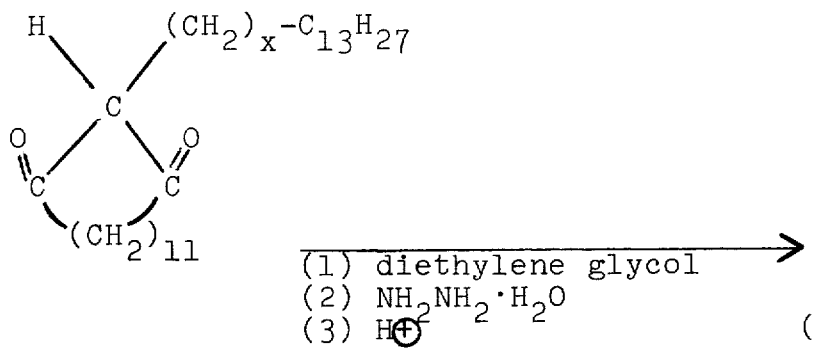

(1) diethylene glycol
(2) $NH_2NH_2 \cdot H_2O$
(3) $H^+$ (III)

Signed and Sealed this

Eighth Day of January 1985

[SEAL]

Attest:

GERALD J. MOSSINGHOFF

Attesting Officer

Commissioner of Patents and Trademarks